United States Patent
Mauger et al.

(10) Patent No.: US 9,100,763 B2
(45) Date of Patent: Aug. 4, 2015

(54) DETERMINING STIMULATION SIGNAL STRENGTH IN AN AUDITORY PROSTHESIS

(75) Inventors: Stefan J. Mauger, Macleod (AU); John M. Heasman, Albert Park (AU); Adam A. Hersbach, The Patch (AU)

(73) Assignee: Cochlear Limited, Macquarie University (AU)

( * ) Notice: Subject to any disclaimer, the term of this patent is extended or adjusted under 35 U.S.C. 154(b) by 539 days.

(21) Appl. No.: 13/564,961

(22) Filed: Aug. 2, 2012

(65) Prior Publication Data

US 2014/0037098 A1 Feb. 6, 2014

(51) Int. Cl.
*H04R 29/00* (2006.01)
*H04R 25/00* (2006.01)
*A61N 1/36* (2006.01)
*A61N 1/05* (2006.01)

(52) U.S. Cl.
CPC .......... *H04R 25/554* (2013.01); *A61N 1/36032* (2013.01); *A61N 1/0541* (2013.01)

(58) Field of Classification Search
CPC . H04R 25/554; A61N 1/36032; A61N 1/0541
USPC ........................... 381/60, 23.1, 312, 315, 317
See application file for complete search history.

(56) References Cited

U.S. PATENT DOCUMENTS 6,205,360 B1 * 3/2001 Carter et al. .................... 607/57

OTHER PUBLICATIONS

Kostas Kokkinakis et al.; A channel-selection criterion for suppressing reverberation in cochlear implants; Department of Electrical Engineering, The University of Texas at Dallas, Richardson, Texas 75080; Journal of Acoustical Society of America 129(5), May 2011, pp. 3221-3232.

* cited by examiner

*Primary Examiner* — Paul S Kim
(74) *Attorney, Agent, or Firm* — McDonnell Boehnen Hulbert & Berghoff LLP (57) ABSTRACT

A method for determining the level of stimulation signals generated by an auditory prosthesis as a result of processing an electrical audio signal representative of sound is disclosed, the method comprising: converting the audio signal into a plurality of frequency-based signal components; analyzing one or more of the signal components to determine a quantity associated with the presence of a target signal in the analyzed signal component; and calculating the signal level based on the determined quantity when the determined quantity indicates a target signal is sufficiently present in the audio signal.

25 Claims, 6 Drawing Sheets

DETERMINING STIMULATION SIGNAL STRENGTH IN AN AUDITORY PROSTHESIS

BACKGROUND

The present technology relates generally to auditory prostheses, sound, and more particularly, to determining stimulation signal strength in an auditory prosthesis.

Auditory prostheses include, for example, hearing aids, middle ear implants, cochlear implants, brain stem implants, auditory mid-brain implant and other totally or mostly implanted devices which provide acoustic, mechanical and/or electrical stimulation to a recipient to assist with hearing. For example, a conventional cochlear implant includes an external unit containing a microphone, sound processor and a transmitter; and an internal or implanted unit containing a receiver/stimulator component and an electrode assembly component. Sound is received at the microphone, which generates electrical audio signals representative of the received sound. The electrode audio signals are processed by the sound processor to generate control signals according to an implemented sound processing strategy for controlling the generation of stimulation signals which are to be delivered to the cochlea via the electrode assembly. The control signals are transmitted by the transmitter to the implanted receiver/stimulator component, which sends corresponding stimulation signals to appropriate electrode contacts of the electrode assembly to stimulate the recipient's auditory nerve to cause a perception of hearing.

Attempts are being made to improve recipient perception of certain target signals, e.g. speech, music and the like. Traditionally, to improve the performance of the auditory prosthesis operating in noise environments, noise reduction algorithms have been used to remove noise from a received signal, such that only a target signal or signal having low noise remains. Other traditional approaches select frequency channels based on the signal-to-noise ratio (SNR). In these and other traditional approaches the amplitude of the acoustic signal is used to determine the corresponding stimulation signal strength.

SUMMARY

In one aspect of the present disclosure, a method for determining the level of stimulation signals generated by an auditory prosthesis as a result of processing an electrical audio signal representative of sound is disclosed, the method comprising: converting the audio signal into a plurality of frequency-based signal components; analyzing one or more of the signal components to determine a quantity associated with the presence of a target signal in the analyzed signal component; and calculating the signal level based on the determined quantity when the determined quantity indicates a target signal is sufficiently present in the audio signal.

In another aspect of the present disclosure, a method of controlling a stimulation signal delivered by an electrode assembly of an auditory prosthesis to provide a prosthesis recipient a perception of a target signal within a sound signal, the method comprising: receiving an electrical audio signal; generating a stimulation signal by an electrode of the electrode assembly corresponding to a component of the received signal, such that a level of stimulation applied by the electrode assembly does not correspond to the acoustic amplitude of the target signal.

In another aspect of the present disclosure, a method of processing a signal to generate control signals for controlling the stimulation of an electrode in an electrode assembly of an auditory stimulation device is disclosed, the method comprising: receiving an electrical audio signal; processing a plurality of frequency-based signal components of the audio signal; and generating a control signal to control stimulation signals delivered by of a plurality of electrodes of the electrode assembly corresponding to the plurality of processed signal components of the signal, wherein the relative stimulation levels of a first and second signal components is not related to the relative acoustic amplitudes of the first and second signal components.

BRIEF DESCRIPTION OF THE DRAWINGS

Illustrative embodiments of the present technology will now be described by way of non-limiting examples only, with reference to the accompanying drawings, in which.

DETAILED DESCRIPTION

Figure 1A:
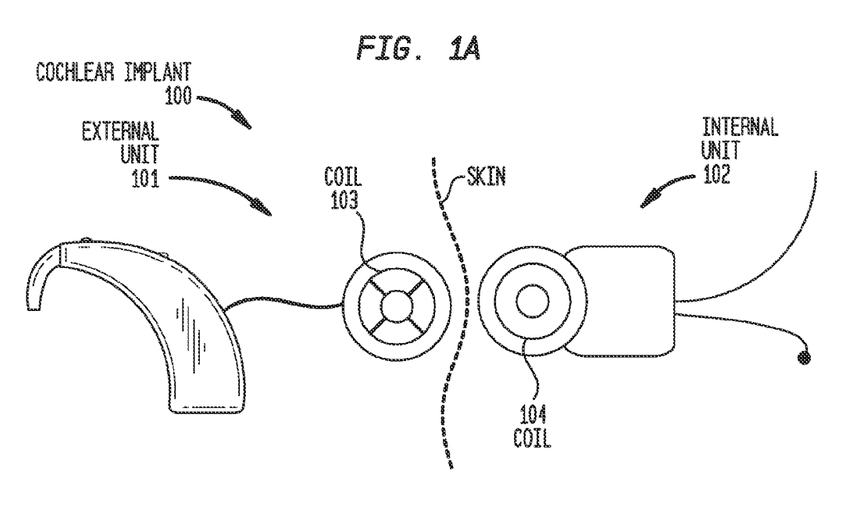
FIG. 1A is a simplified perspective view of an exemplary auditory prosthesis, namely, a cochlear implant, in which embodiments of the present technology may be implemented.
Figure 1B:
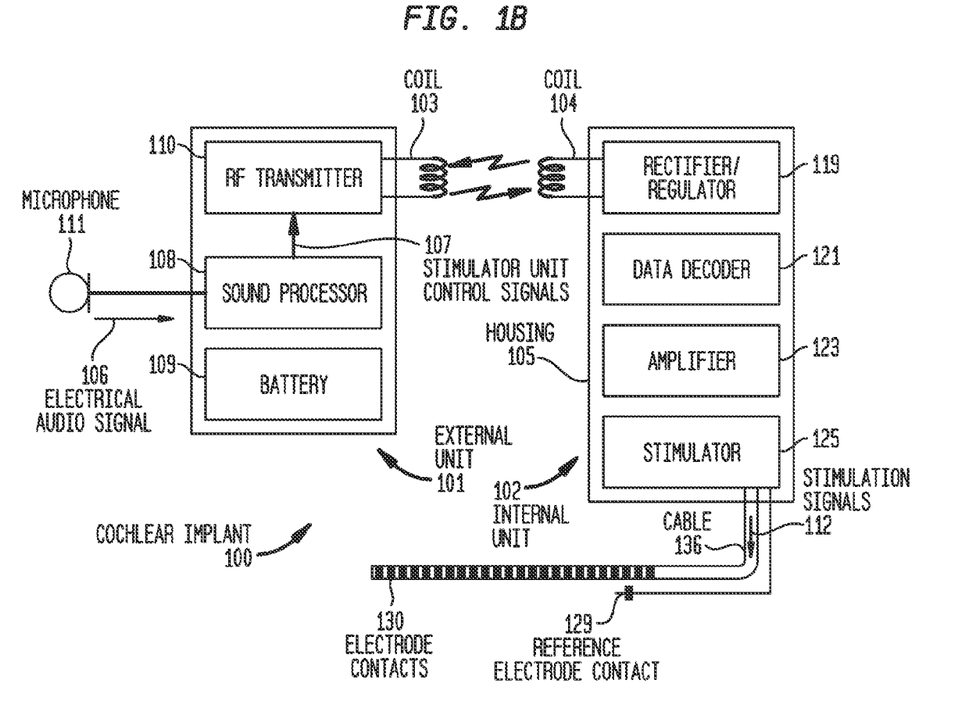
FIG. 1B is a simplified functional block diagram of an embodiment of the auditory prosthesis of FIG. 1A.

FIG. 1A is a simplified perspective view of an exemplary auditory prosthesis, namely, a cochlear implant 100, in which embodiments of the present technology may be implemented. FIG. 1B is a simplified functional block diagram of cochlear implant 100 illustrated in FIG. 1A. For the purposes of clarity of illustration, the present technology will be described primarily with reference to its implementation in this form of auditory prosthesis. However, the technology may also be implemented in other auditory prostheses. For example, the technology may be implemented in a totally implantable cochlear implant, in which the functions of the external units are incorporated into the implantable unit.

Cochlear implant 100 includes an external unit 101 and an internal unit 102 for implantation in a recipient. External unit 101 includes a microphone and sound processor for receiving sounds, and in response generates control signals for transmission via an induction coil 103. Implanted unit 102 includes an induction coil 104 to receive the transmitted control signals and a stimulator 125 that generates stimulation signals based on the received control signals.

External unit 101 has a sound input device such as microphone 111 for receiving acoustic sound and for generating electrical audio signals 106 representing the received sound. It should be appreciated that components other than microphone 111 which generates electrical audio signals, such as a telecoil, date recorder, etc. A sound processor 108 processes the audio signals produced by microphone 111 and generates control signals 107 for controlling the stimulation signals delivered by internal unit 102. External unit 101 also includes a radio frequency (RF) transmitter 110 coupled to external coil 103. Transmitter 110 generates an alternating current in coil 103, which inductively couples with an implanted coil 104 of internal unit 102. The inductive link formed by induction coils 103, 104 may also function to transfer power from external unit 101 to internal unit 102, and to transfer telemetry data from internal unit 102 to external unit 101.

Internal unit 102 includes an induction coil 104 for receiving the RF transmission, a rectifier and regulator 119 that rectifies and regulates the received RF signal, a data decoder 121 extracts control signals 107 and other data encoded in received RF signal, and an amplifier 123 drives a stimulator 125 based on the decoded data. Stimulator 125 generates stimulation signals 112 in response to control signals 107, and delivers the stimulation signals to the recipient via electrode contacts 130 to stimulate the auditory nerve of the cochlea. Implanted unit 102 also includes a hermetic housing 105 to protect the circuitry. Stimulation signals 112 are communicated via a cable 136 of insulated wires to electrode contacts 130. Electrode contacts 130 are arranged in an array, in this embodiment as a linear array suitable for insertion into the cochlea. Implanted unit 102 also includes a reference electrode contact 129. Electrode contacts 130 and their associated insulated wires may be made from platinum or other conductive materials.

Because the cochlea is tonotopically mapped, each electrode contact 130 of the electrode assembly can be arranged to deliver stimulating signals 112 to a particular region of the cochlea. In the representation of sound as electrical stimulation, frequencies are allocated to individual electrode contacts 130 of the electrode assembly. This enables auditory prosthesis 100 to deliver electrical stimulation signals 112 to selected auditory nerve fibers, thereby allowing the brain to perceive hearing sensations resembling natural hearing sensations. In achieving this, processing channels of sound processor 108, that is, specific frequency bands with their associated signal processing paths, are mapped to a set of one or more electrode contacts to stimulate a desired nerve fiber or nerve region of the cochlea.

Figure 2:
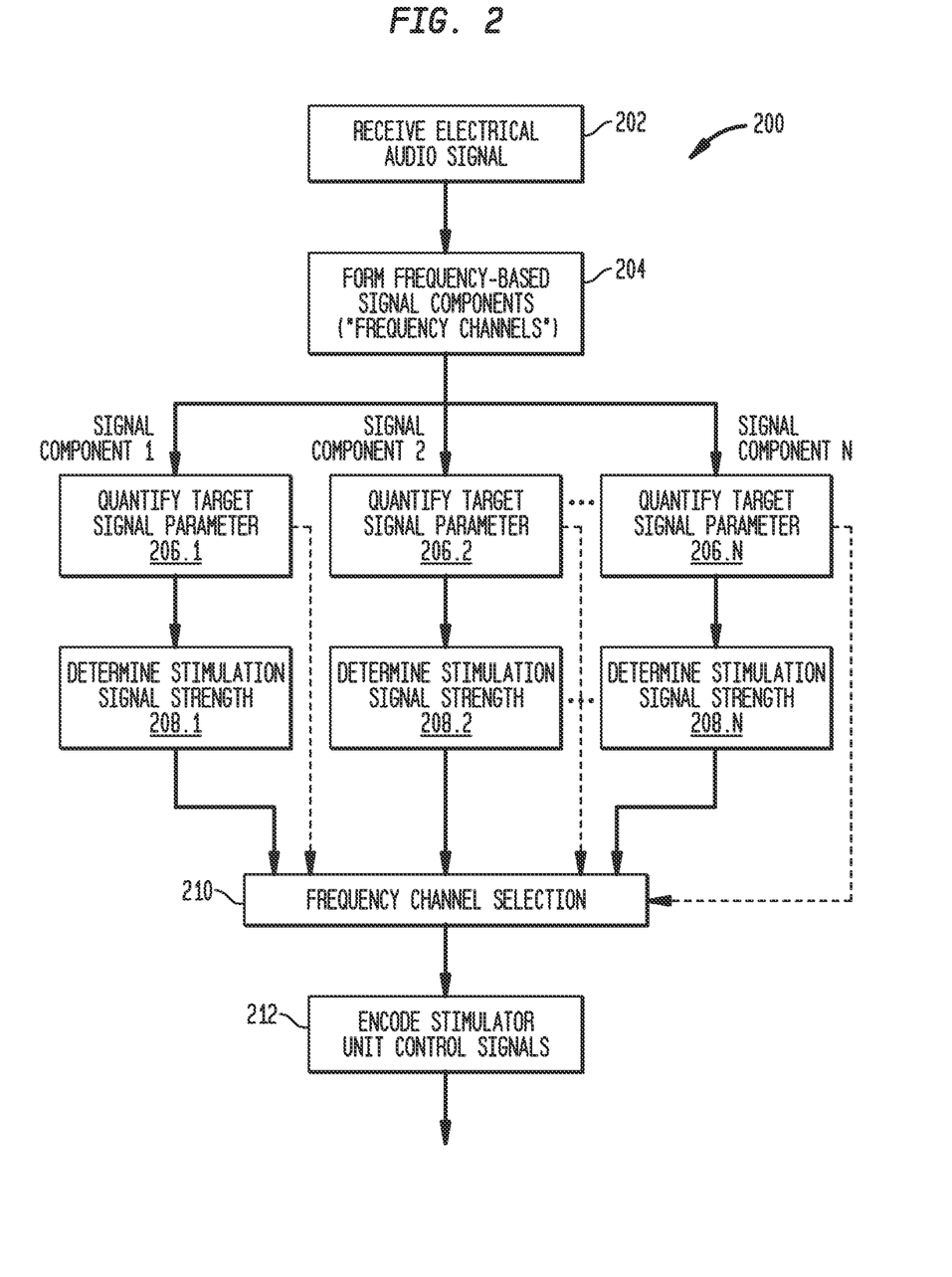
FIG. 2 is a flow chart of an embodiment of a multi-channel process for generating stimulation control signals.

FIG. 2 is a flow chart of an embodiment of a multi-channel process 200 implemented in an auditory prosthesis sound processor such as sound processor 108 for generating stimulation control signals 107 that cause stimulator 125 to generate stimulation signals 112 having a signal level or strength determined during process 200. The stimulation level or strength for a signal component is determined by the charge level delivered by the signal. This can be achieved by varying the amplitude or width of the stimulation pulse, rate of stimulation or interphase gap of the stimulation signals applied by the electrode contact.

Process 200 begins at block 202 with the receipt of an electrical audio 106 signal by sound processor 108. As noted, such an electrical audio signal may be generated by microphone 111 or other sound input device such as a telecoil, computer, telecommunications device, or other electrical device capable of transmitting a signal that represents sound.

At block 204, electrical audio signal 106 is converted into a plurality of signal components which will be used for further analysis. In certain embodiments, the operations performed at block 304 include digitally sampling the analog electrical audio signal using, for example, an analog-to-digital converter (ADC). The signal samples are buffered with some overlap and then windowed prior to generation of a frequency domain signal by Fast Fourier Transform (FFT). This frequency domain conversion could be performed using a wide variety of mechanisms including but not limited to a Discrete Fourier Transform (DFT). The frequency domain conversion generates complex valued frequency domain representations of the electrical audio signal in a plurality of frequency bins (FFT bins). The FFT bins can then be combined e.g., by power summation, to provide the required number of frequency channels (signal components) to be processed by sound processor 108.

In some embodiments, the ADC sampling rate is 16 kHz and the resulting signal samples are stored in a 128 sample buffer with a 96 sample overlap. In one embodiment, the windowing is performed using a 128 sample Hanning window. In the same or alternative embodiment, a 128 sample fast Fourier transform is performed. The results of the FFT operations are summed to provide, in one example, a quantity of frequency channels that is the same as the quantity of electrode contacts so that one frequency channel is associated with one electrode contact.

Each frequency channel, or signal component, is processed to determine control signal(s) 107 which are to be used by stimulator 125 to generate stimulation signals 112 for delivery to the cochlea via a corresponding electrode contact 130. The general process of determining the control signal(s) for each frequency channel will follow a similar overall scheme. However, in some embodiments, the above processing of the frequency channels will vary.

The processing of each frequency channel occurs in a series of steps represented by vertically-aligned blocks in FIG. 2. Note that equivalent blocks of each such column are denoted with the same reference number prefix followed by a sequential suffix such as 0.2 to .n, as appropriate. At block 206, a signal component is processed to determine a quantity which is related to, or correlated with, the presence of a target signal within that signal component. Such a quantity may be, for example, the output of a voice activity detector which determines the presence or absence of speech in the processed signal component. Another example is the amplitude of the signal component relative to another signal component, or group of signal components. The determined quantity is used in block 308.1 (and 208.2 to 208.n) to determine the signal strength of the stimulation signal generated for the electrode contact corresponding to that signal component. As will be appreciated from the following description, the stimulation level for a signal component can be determined in a variety of ways. In one embodiment, the stimulation level of the signal component is a predetermined, fixed or quantized stimulation level that will be used if the target signal is present and/or depending upon the parameter value determined at block 206.

In another embodiment, the stimulation level is a random stimulation level that will be used if it is determined that the target signal is present on the basis of the calculation of the parameter value at block 206. The random stimulation level may be determined within a predefined stimulation level range for the signal component. In another embodiment, the stimulation level is determined according to a function of the value calculated in step 206.

At block 210, the frequency channels for which stimulation signals 112 will be generated are selected. For example, there may be a limit on the number of electrode contacts 130 which can be stimulated simultaneously, or in one time slot. One such scheme is known as an N of M selection strategy in which N channels of a possible M electrode contacts 130 are selected for stimulation in any single time period. In this example, the channel selection may also be based on the parameter value calculated at block 206 for each of the frequency channels. In an alternative embodiment, the frequency channel selection may be based on the determined simulation strength in block 208.

Once the frequency channels are selected at block 210, control signals 107, which are necessary to drive stimulation 125 to generate stimulation signals 112, are encoded at block 312 for transmission to internal unit 102.

The quantity used in blocks 206.1 to 206.$n$ which is related to, or considered to be correlated with, the presence of a target signal is a quantity that represents a characteristic of either the target signal itself or the signal component as a whole which is believed to be correlated with the presence of the target signal, referred to herein as a target signal parameter. The quantity could be determined on the basis of different analysis techniques.

For example, in one embodiment, a statistical analysis of the signal component is performed to determine the target signal parameter. The statistical analysis of the signal component and one or more additional signal components or the whole signal, can be made to determine a measure of the relative loudness of the target signal compared to a non-target signal. Such methods create a plurality of dynamic measures of the signal component. One signal component measurement reflects the target signal and the other signal component measurement(s) reflect non-target signal. These dynamic measures can then be used together to determine relative loudness of the target signal compared to the non-target signal.

The starting point for methods of this type can be the raw electrical audio signal, a smoothed electrical audio signal or a noise-reduced electrical audio signal which is then processed to determine the two dynamic measures. In one example, the dynamic measure of a non-signal target component could include performing a long-term signal average of the entire signal component, performing a signal minimum tracking method or performing a noise estimation method on the signal component. If the relative loudness of the two dynamic measures meets some predetermined criteria, e.g. the relative signal loudness of the target signal is above a predetermined threshold, it can be determined that the target signal is present, or sufficiently strong that a control signal can be produced. Alternatively, rather than making a binary decision on the basis of the quantity calculated, the relative loudness quantity can be used directly in determining the stimulation level of the corresponding control signal.

In another embodiment, phase analysis of received signal is performed. In these methods the phase of one or more spectral components output from the FFT process performed at block 304 can be analyzed, e.g. over time or across multiple FFT bins, to determined the presence of a target signal.

In another embodiment, target signal probability analysis is performed. In these methods, the probability that a target signal, e.g. speech or music or other target signal, is present in the signal component is determined by analyzing at the signal over time and across multiple frequency channels. Such methods include voice activity detection, minimum tracking methods, histogram methods and subspace methods.

Each of these methods produces an internal measure of the target signal presence. This value can be used as an indication of the probability that the target signal is present in the signal component. As noted in the previous example, this value can be used as part of a binary decision making process to determine whether the target signal is present or be used directly to control stimulation level for the control signal corresponding to the signal component.

In an alternative embodiment, target signal informational analysis of the received signal component is performed based on an application of information theory techniques. In these methods, the quantity of information present in the target signal is determined using techniques such as entropy analysis of the signal, mitral information, informational divergence and statistical coding theory. Such methods can be used to analyze the received signal component and extract the informational content of the target signal. As noted above, this value can then be used either as part of a decision making process or to directly determine stimulation level.

In another embodiment, heuristic target signal analysis techniques are applied to one or more signal components or quantities derived therefrom or other inputs to the auditory prosthesis to determine a quantity that indicates a likelihood of the target signal being present in a signal component. The heuristic analysis can use a series of rules or different analysis techniques which then may be combined to determine the presence of the target signal within the signal component. The heuristic analysis techniques can include genetic algorithms, clustering and fuzzy logic. The heuristic methods applied to each frequency channel are used to judge whether the information they contain are either related to the target signal, or a target signal in an associated frequency channel. Based on these judgments, frequency channels can be weighted appropriately such that either individual or clustered groups of frequency channels can have control signals generated which enhance the saliency of target signals in each signal component.

Figure 3A:
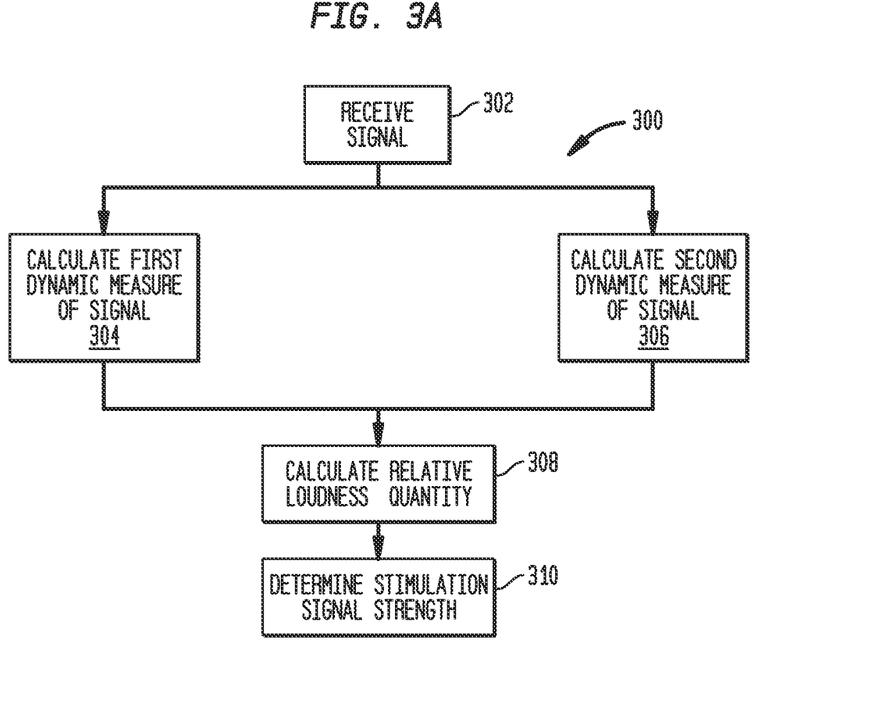
FIG. 3A is a flow chart illustrating an exemplary method of generating a control signal based on a relative loudness of a target signal compared to a non target signal.

FIG. 3A is a flow chart of a process 300 that is performed to determine stimulation signal strength. Process 300 uses the relative loudness of the target signal within the signal component compared to another portion of the signal component to determine the stimulation level of the control signal. Process 300 begins by receiving an incoming signal at block 302 which is an electrical signal representing the component of the signal to be reproduced by the electrode. The incoming signal is processed at block 304 to determine a first dynamic measure of a target signal within the signal component. The incoming signal is also processed at block 306 to create a second dynamic measure of the signal. However, at block 306 the dynamic measure is calculated for a different portion of the received signal than is used in step 304. For example, the portion of the incoming signal processed at block 306 may be a noise component of the incoming signal, whereas the signal processed in block 304 may just be the incoming signal or noise reduced signal component.

The target signal used at block 304 can be determined by smoothing the incoming signal, or using a noise reduced version of the incoming signal which has had its noise component removed according to conventional noise reduction methods. The non-target signal can be created by performing a process such as determining a long-term signal average of the incoming signal, tracking the minimum of the incoming signal or by performing conventional noise estimation methods on the incoming signal. The results of the operations performed at blocks 304 and 306 are combined to produce a relative measure of the target signal statistics compared to the non-target signal statistics.

In one embodiment, the signal to noise ratio (SNR) of the received signal component is calculated by comparing the relative loudness of the entire signal to that of its noise component as follows:

$$SNR = \frac{Signal}{NoiseEstimate} - 1.$$

Figure 3B:
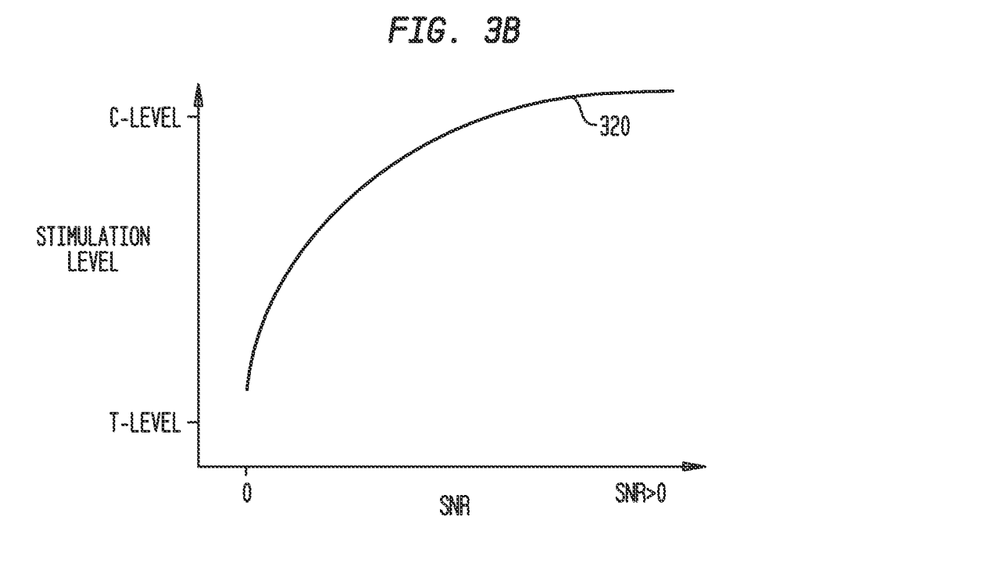
FIG. 3B illustrates a curve that can be used in an exemplary implementation of the method of FIG. 2 to set the stimulation level on the basis of a relative loudness measure of the analyzed signal component.

If the incoming signal has a high signal-to-noise ratio, this can imply that the incoming signal has a suitable target signal irrespective of what that target signal represents, i.e. a signal component which is largely unaffected by noise, as opposed to any specific signal of interest such as a speech signal. In this case, the present method determines that this property indicates that stimulation of an electrode contact should be performed. The output of the relative loudness calculation block 308 is used in block 310 to determine stimulation level of the stimulation signal 112 to be applied to the corresponding electrode contact of the electrode assembly. FIG. 3B illustrates a mechanism by which a relative loudness measure, signal-to-noise ratio (SNR), can be used to map the stimulation level encoded in the stimulation signal. FIG. 3B illustrates a plot of a curve 320 mapping signal-to-noise ratio to stimulation signal strength. As can be seen, for signals where the SNR is above the threshold, (for example, 0 dB in FIG. 3B) the stimulation level is set according to curve 320. As can be seen, at the lowest SNR value, 0 dB, a low stimulation level is applied. For a signal component having a relative loudness measure lying at the lower stimulation threshold (at which it is determined that the target signal is present), the stimulation signal will have a stimulation level equal to the threshold level (T-level) of the recipient. The stimulation signal strength of the stimulation signal can be increased with increasing relative loudness of the target signal towards the C-level of the device recipient. As will be appreciated, the threshold level at 0 dB is purely illustrative and other starting thresholds may be used. Moreover, the function used to set the stimulation level above the threshold may take any desired form. For example, the equation may be defined in a piece-wise function such that quantised stimulation levels are applied with stimulation level being fixed for a relative loudness within predefined ranges.

Figure 4A:
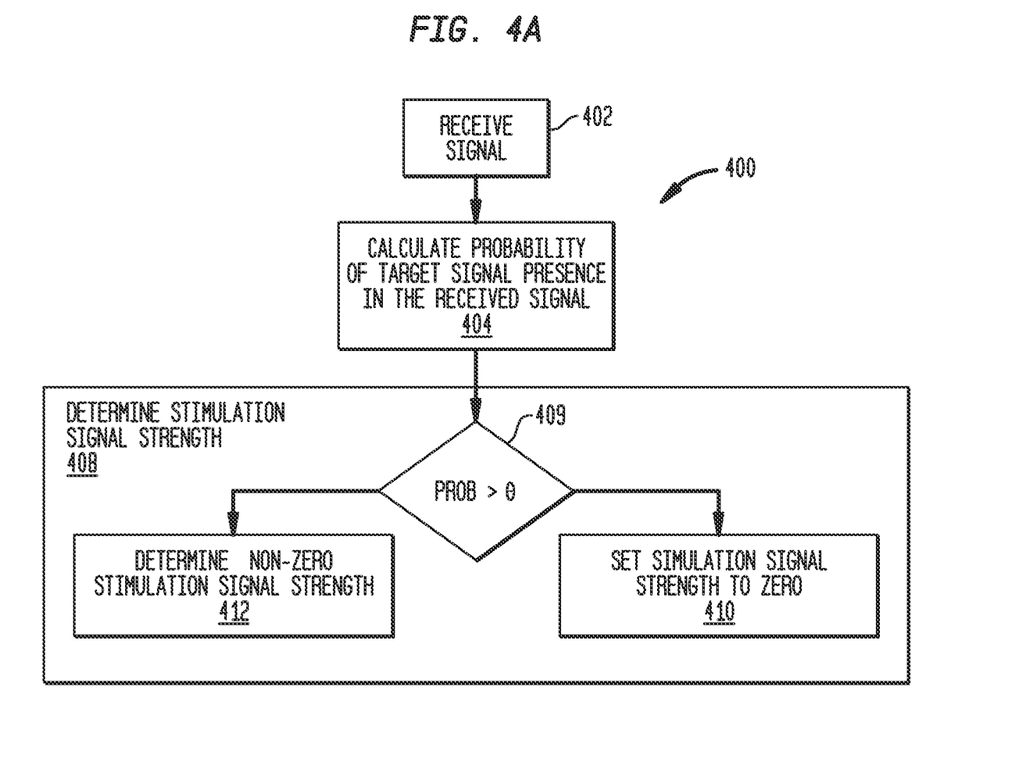
FIG. 4A is a flow chart illustrating an exemplary method for determining the probability that a target signal is present in a received electrical audio signal, and to determine the strength of the stimulation signal.

FIG. 4A is a flow chart illustrating an exemplary process 400 for stimulating an electrode contact of an auditory prosthesis in which the stimulation level is determined according to the probability of the presence of a particular target signal in the signal component. Method 400 begins by receiving an incoming signal at block 402. The incoming signal is analyzed at block 404 to determine the quantity which represents a likelihood that the target signal is present within the incoming signal. The operation of block 404 may be performed by performing voice activation detection on the incoming signal to determine whether speech is present. Alternatively, minimum tracking methods, histogram methods or subspace methods can be used to determine the presence of some particular target signal within the incoming signal. The result of the operations performed at block 404 is a probability value between 0 and 1 indicating the likelihood that the target signal is present in the incoming signal component.

Figure 4B:
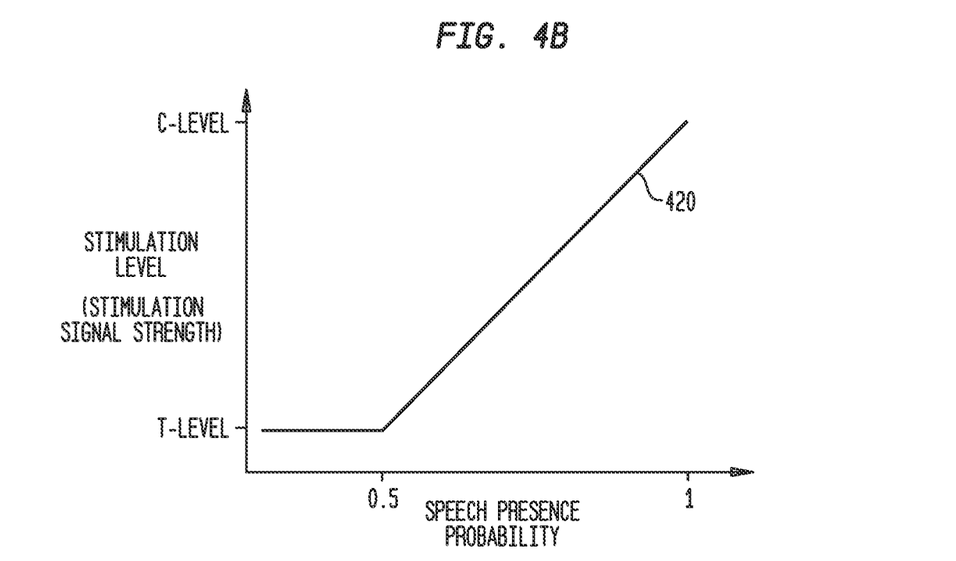
FIG. 4B illustrates a curve that can be used in exemplary implementation of the method of FIG. 4A to set the stimulation signal strength on the basis of the probability that a target signal is present in the analyzed signal component.

The probability value determined at block 404 can be used in a variety of ways in order to determine the strength of the stimulation signal corresponding to the signal component. In the present example, the process for determining stimulation signal strength at block 406 includes an initial thresholding operation at decision block 409 at which the target signal probability measure is compared with the threshold θ to determine whether the target signal is present. In the event that the target signal is insufficiently likely to be present, i.e. probability is less than θ, the stimulation level for the stimulation signal is set to zero at block 510. However, in the event that the probability that the target signal is present is above the threshold level, a non-zero stimulation level can be determined. One method of doing this is illustrated in the graph of FIG. 4B. As can be seen by curve 520, for a speech presence probability of less than 0.5, the stimulation level is set at below the recipient's T-level, effectively meaning that the stimulation will not result in a hearing percept. However, the stimulation signal strength increases linearly from the T-level to the C-level as the speech presence probability increases from 0.5 to 1. Other thresholds and non-linear mappings may also be used.

Accordingly, stimulus strength in this example can be written according to the piecewise function.

$$\text{Stimulus level} = \begin{cases} \left(\frac{p-\theta}{1-\theta}\right), & p > \theta \\ 0, & p \leq \theta \end{cases}$$

where p is the calculated probability value and θ is the threshold below which no target signal is considered to be reliably detectable. An alternative to this method in which the probability is used to scale stimulation level directly is to use a random stimulation level if the target signal presence probability exceeds the threshold probability. This can be represented as follows:

$$\text{Stimulus level} = \begin{cases} rand[0.5, 1], & p > \theta \\ 0, & p \leq \theta \end{cases}$$

where p is the calculated probability value and θ is the threshold below which no target signal is considered to be reliably detectable. When p is greater than θ a random stimulation level is applied that lies in the range of between the recipient's T-level and C-level for the relevant frequency channel.

Alternatively, a fixed stimulation level can be applied. In this example for a probability less than the switch-on-threshold probability θ, stimulation level of 0 is applied, whereas above the threshold level, a fixed stimulation of some value between the T-level and C-level for the recipient can be used. This can be represented as follows:

$$\text{Stimulus level} = \begin{cases} 1, & p > \theta \\ 0, & p \leq \theta \end{cases}$$

The fixed level may be set at a different level if desired e.g. half way between the recipient's T- and C-levels. In other examples, a multiple quantised stimulation levels can be assigned to different corresponding probability ranges, e.g. as follows:

$$\text{Stimulus level} = \begin{cases} 1 & p > \vartheta_2 \\ 0.75 & \vartheta_2 \geq p > \vartheta \\ 0 & p \leq \vartheta \end{cases}$$

where θ is the stimulation cut-off threshold and $\theta_2$ is a threshold over which a higher stimulation level is applied.

Figure 5A:
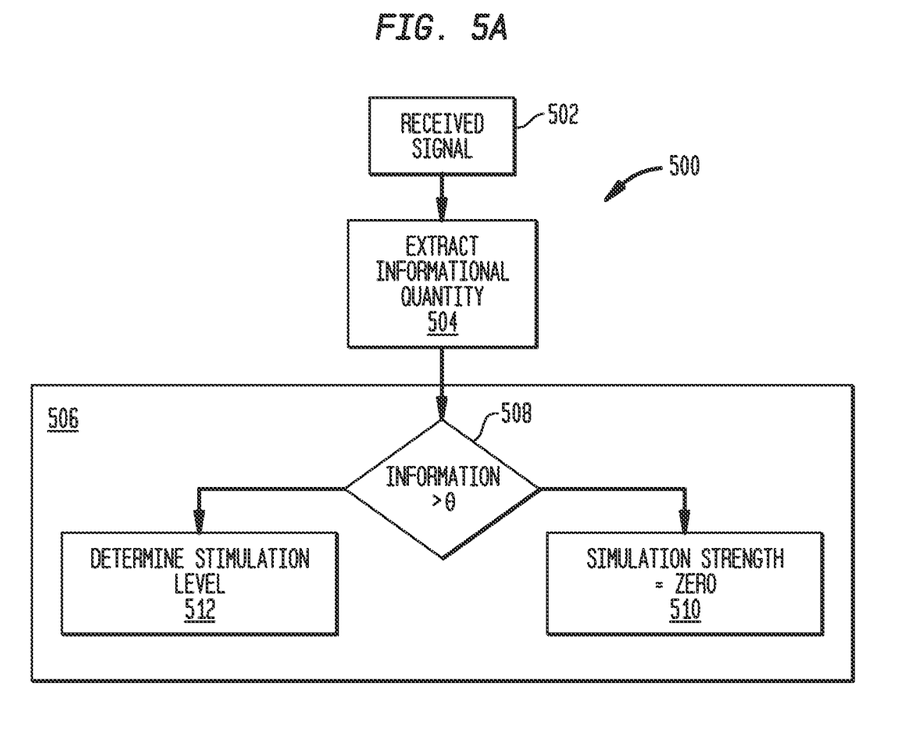
FIG. 5A is a flow chart illustrating a further method for generating a control signal which uses the informational content of the received electrode and signal in order to determine the stimulation strength of the control signal to be applied at the electrode.
Figure 5B:
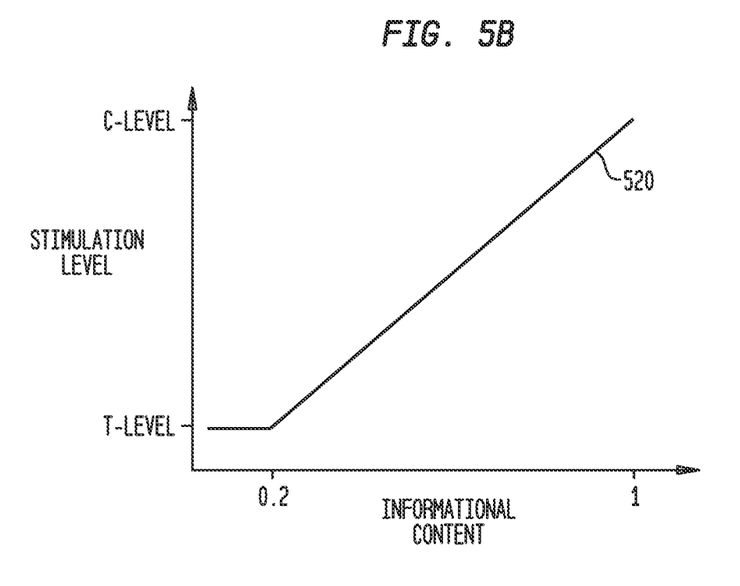
FIG. 5B illustrates a curve that can be used in exemplary implementation of the method of FIG. 5 to set the stimulation level of a control signal on the basis of an informational quantity associated with the analyzed signal component.

FIG. 5A illustrates an exemplary process for using informational theory analysis of the incoming signal to determine the stimulation level encoded in stimulation signal to control an electrode of an auditory stimulation device. As with the previous examples, the method 500 begins with receiving an incoming signal at block 502. The incoming signal represents a signal component within a fixed frequency band. In block 504, the signal is analyzed to quantify the informational content of the incoming signal. The informational content can be determined by analyzing signal entropy, mutual information or informational divergence or use statistical coding theory to determine a measure of the informational content of the incoming signal. At block 506 the stimulation level is determined. This can be performed, for example, by comparing the information quantity to a predetermined threshold. The threshold could be a predetermined value, or dynamic value created from analysis of the incoming signal over time. For example, an average long-term information level could be determined and used as the threshold. At block 508 the quantity of information content is compared to a threshold and if the threshold is not exceeded, then at block 510 the stimulation level is set to zero. Alternatively, if the quantity of informational content exceeds the threshold, then stimulation level can be determined according to a pre-set algorithm. For example, the stimulation level could be a fixed stimulus level, a random stimulus level or a stimulus level determined as a function of the informational quantity of interest within the signal. FIG. 5B illustrates an example of a stimulus setting algorithms. In this example, stimulus strength to be applied to a frequency channel is defined as follows:

$$\text{Stimulus level} = \begin{cases} \left(\frac{i-\vartheta}{1-\vartheta}\right), & i > \vartheta \\ 0, & i \leq \vartheta \end{cases}$$

where θ is the stimulation cut-off threshold and i is the current value of the information measure for the channel. In this example, if the informational content measure i is between 0.2 and 1, the stimulation strength applied is set according to curve 520 and increases from the T-level of the recipient to the C-level of the recipient as i ranges from 0.2 to 1. Below 0.2 the stimulation strength is less than T-level of the recipient and the channel is effectively left unstimulated.

Figure 6A:
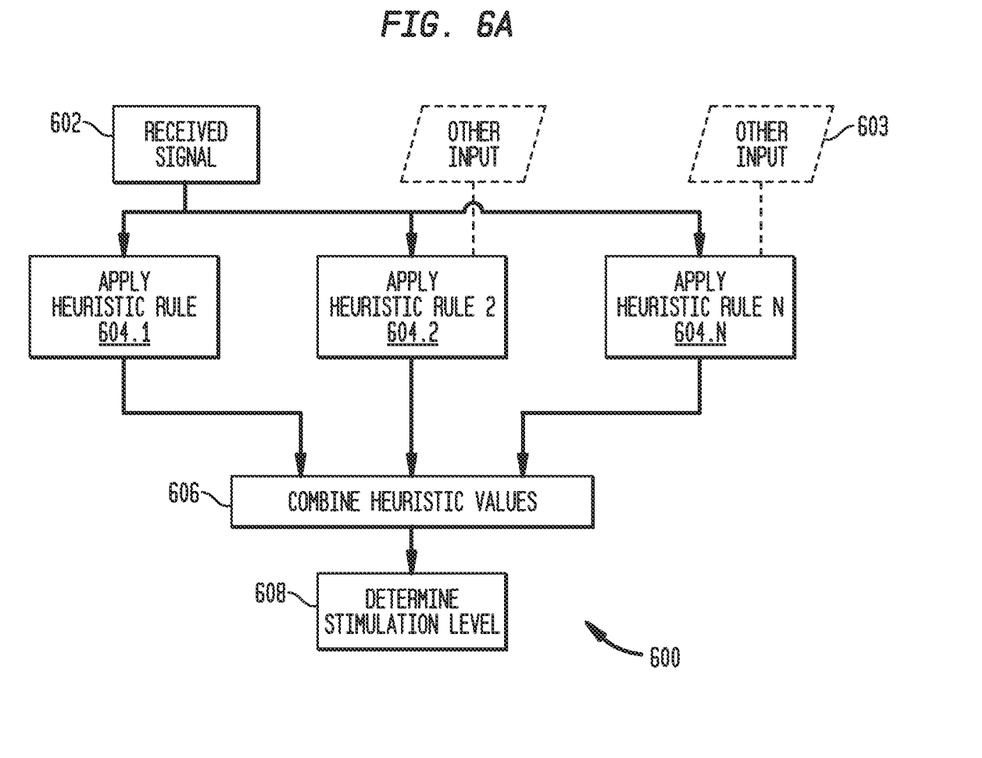
FIG. 6A illustrates a process for generating a control signal for controlling the stimulation of an electrode, or more than one electrode of an auditory stimulation device using one or more heuristic rules to determine stimulation strength of the control signal.

FIG. 6A illustrates a process 600 for using heuristic analysis of an incoming signal to determine stimulation level for its corresponding electrode. The heuristic analysis method begins by receiving the incoming signal at block 602. This signal is then processed according to a plurality of heuristic rules 604.1 to 604.n to determine the plurality of heuristic rule output values.

The heuristic rules may involve processing the incoming signal as described in any of the previous examples to determine one or more quantities relating to the presence of the target signal in the signal component. However, the heuristic rules may also have inputs from frequency channels other than the present frequency channel, or receive other inputs 603 from the recipient or prosthesis usage history that can be used in the heuristic analysis to determine the likelihood of a target signal being present in the incoming signal. For example, a heuristic rule may exist which compares the incoming signal in the present channel to the incoming signal a related channel and if the comparison fits predetermine pattern, the heuristic rule may determine that a target signal is present in the group of channels. For example, speech may be recognized by certain temporal and frequency characteristics across a range of channels or frequencies within a channel, and if characteristics indicative of the presence of speech appear in one or more of a group of related channels, it may be determined that speech is also present in another channel, even though that other channel does not display the necessary frequency or temporal characteristics. Another example of this may be present when listening to music whereby a musical instrument will generate sound at a fundamental pitch but harmonics are also present. In this case, detection of a high amplitude or low SNR component in a channel may cause a determination to be made that another channel should be stimulated at a certain level, as it is likely to contain a harmonic of that fundamental pitch, irrespective of the other channel's amplitude or other characteristics. Another example might use temporal analysis of the present channel. It may be determined that a sudden departure of the present channel from its long-term average characteristic should result in a high likelihood of stimulating the electrode to represent the sudden change in sound in the particular channel. For example, if a channel has been relatively noisy over a long period of time and suddenly the signal-to-noise ratio of the channel increases markedly, although not to a level which would ordinarily trigger stimulation using a relative loudness method, it may be determined that a new source of a target signal has arisen in the channel and thus stimulation of the electrode corresponding to the particular channel should preferentially be performed.

Figure 6B:
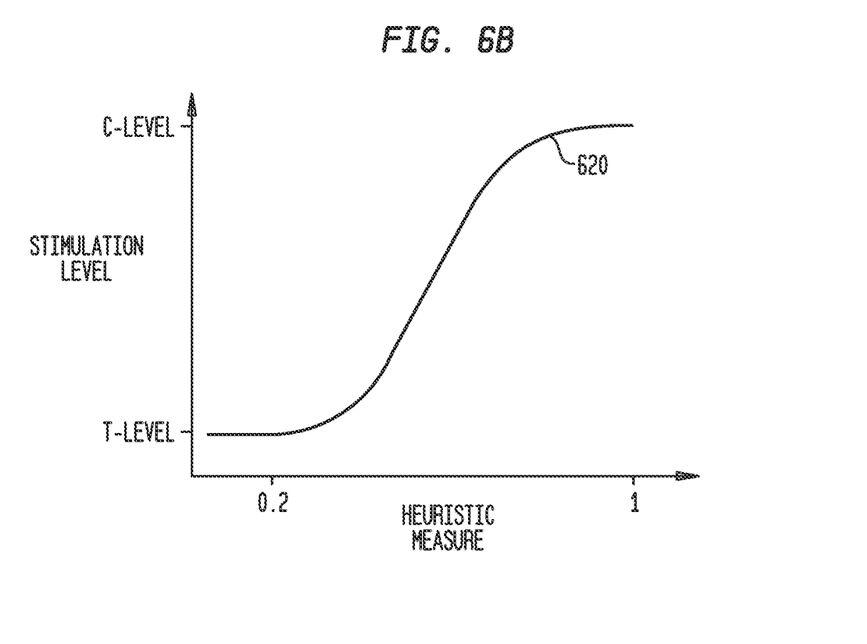
FIG. 6B illustrates a curve that can be used in exemplary implementation of the method of FIG. 6A to set the stimulation level on the basis of a heuristic analysis of the analyzed signal component.

At block 706 the results of the application of a plurality of heuristic rules are combined to deliver an overall value corresponding to the signal component. This value can then be used to determine stimulation level in block 708. FIG. 6B illustrates a stimulus level curve which may be used in step 710. In this example, a stimulation level curve is defined which increases from T-level to C-level as the heuristic measure moves between 0.2 and 1. Below the 0.2 level no stimulation will occur as the stimulation level is determined to be below the recipient's T-level. The frequency/temporal analysis, and other rule based heuristic analysis in steps 704.1 to 704.n, as well as the combination step 708, may be performed in a wide variety of ways including application of genetic algorithms, clustering, fuzzy logic or artificial neural net selection processes.

Embodiments may be implemented in bilateral auditory stimulation systems comprising two auditory stimulation devices that communicate with each other. In such bilateral system the two auditory stimulation devices can operate independently or cooperatively to determine the presence of a target signal. In the independent operation case, the methods described above are used independently in each auditory stimulation device. In the cooperative case, the auditory stimulation devices communicate data indicating the presence of a target signal to each other. Each auditory stimulation device then uses received data indicating the presence of a target signal in addition to its own determination of the presence of a target signal to determine the presence of the target signal. For example, a target signal may be strongly identified by one of the auditory stimulation devices, whereas it is weakly detected or not detected by the other—this could occur in the case of a sound coming from a highly localised source in a certain direction. In one mode of operation, if the detection by the one of the auditory stimulation device is stronger than a detection threshold, the auditory stimulation device that has only weakly identified the target signal is controlled to boost the stimulation level of a channel corresponding to the target signal. In another mode of operation, the strong detection of the target signal by one of the auditory stimulation device is overridden or suppressed by the non detection by the other the auditory stimulation, because it may be determined that the highly directional sound is a noise source to be ignored. Other strategies to share and combine target signal detection data, such as averaging, performing a weighted combination or "double knock" detection strategies can be implemented.

As will be appreciated from the foregoing, in each example, the analysis signal method is based on a determination that a certain characteristic of the sound, that is to be re-created for the implant recipient, can be analyzed to determine whether the received sound (or a component of it) carries useful content that would be advantageous to reproduce. The received signal is analyzed to quantify that characteristic, and that characteristic is then used to determine if, and possibly how strongly, the signal component should be expressed to the recipient. This decision, or the stimulation signal's stimulation level does not reflect the acoustic amplitude of the incoming signal, but reflects the likely level of benefit to be gained by stimulating an electrode corresponding to the signal component.

It will be understood that the technology disclosed and defined in this specification extends to all alternative combinations of two or more of the individual features mentioned or evident from the text or drawings. All of these different combinations constitute various alternative aspects of the technology.

What is claimed is:

1. A method for determining the level of stimulation signals generated by an auditory prosthesis as a result of processing an electrical audio signal representative of sound, the method comprising:
   converting the audio signal into a plurality of frequency-based signal components;
   analyzing one or more of the signal components to determine a quantity associated with the presence of a target signal in the analyzed signal component; and
   calculating the signal level based on the determined quantity when the determined quantity indicates a target signal is sufficiently present in the audio signal.

2. The method of claim 1, wherein the determined quantity is not the acoustic amplitude of the sound or the target signal if the target signal is present in the sound.

3. The method of claim 1, wherein the stimulation level does not represent the acoustic amplitude of the sound nor the target signal if the target signal is present in the sound.

4. The method of claim 1, wherein the method further comprises:
   comparing the determined quantity to at least one predetermined criterion relating to the presence of the target signal in the analysed signal component.

5. The method of claim 4, wherein, in the event that the target signal is determined to be present in the analyzed component of the signal, the method further comprising:
determining a stimulation level to be set by the control signal that is not calculated from the determined quantity.

6. The method of claim 4, wherein the stimulation level is predetermined in the event that the target signal is present.

7. The method of claim 1, wherein the stimulation level is determined according to a function of the quantity that is associated with the presence of the target signal.

8. The method of claim 1, wherein the electrode is an electrode corresponding to the analyzed component of the sound signal.

9. The method of claim 1, wherein the electrode is an electrode corresponding to a component of the signal that is related to the analyzed component of the sound signal.

10. The method of claim 1, wherein the quantity that is associated with the presence of a target signal is a quantity representing a probability of the presence of the target signal in the component of the signal.

11. The method of claim 10, wherein the stimulation level to be applied by the electrode is determined on the basis of the probability of the presence of the target signal in the received signal.

12. The method of claim 1, wherein the determined quantity is a quantity representing the relative loudness of a target signal compared to another signal component.

13. The method of claim 12, wherein the stimulation level to be applied by the electrode is determined on the basis of the relative loudness of the target signal compared to another component in the received signal.

14. The method of claim 1, wherein the determined quantity is determined on the basis of an informational content of the analyzed component.

15. The method of claim 14, wherein the stimulation levels is determined on the basis of the informational content of the analyzed signal component.

16. The method of claim 1, wherein the at least one predetermined criterion includes a plurality of criteria, and the method further comprising:
   applying a heuristic rule to the determined quantity using at least some of the plurality of criteria.

17. The method of claim 1, wherein the target signal is speech.

18. A method of controlling a stimulation signal delivered by an electrode assembly of an auditory prosthesis to provide a prosthesis recipient a perception of a target signal within a sound signal, the method comprising:
   receiving an electrical audio signal;
   generating a stimulation signal by an electrode of the electrode assembly corresponding to a component of the received signal, such that a level of stimulation applied by the electrode assembly does not correspond to the acoustic amplitude of the target signal.

19. The method of claim 18, further comprising:
   determining a stimulation level for a signal component within the received signal that corresponds to the target signal based on one or more of the following:
   a fixed stimulus level;
   a random stimulus level;
   a psychoacoustic model of speech perception;
   a heuristic process;
   an informational metric of the received signal;
   a relative loudness of the signal component compared to another component of the received signal;
   a probability of the presence of a target signal in the received signal.

20. A method of processing a signal to generate control signals for controlling the stimulation of an electrode in an electrode assembly of an auditory stimulation device, the method comprising:
receiving an electrical audio signal;
processing a plurality of frequency-based signal components of the audio signal; and
generating a control signal to control stimulation signals delivered by of a plurality of electrodes of the electrode assembly corresponding to the plurality of processed signal components of the signal, wherein the relative stimulation levels of a first and second signal components is not related to the relative acoustic amplitudes of the first and second signal components.

21. The method of claim 20, wherein the method includes, determining a stimulation level for each signal component based on one or more of the following:
a fixed stimulus level;
a random stimulus level;
a psychoacoustic model of speech perception;
a heuristic process;
an informational metric of the received signal;
a relative loudness of the signal component compared to another component of the received signal;
a probability of the presence of a target signal in the received signal.

22. The method of claim 20, further comprising analyzing each component of the signal and determining a likelihood of the presence of a target signal in the audio signal.

23. The method of claim 20, further comprising:
analyzing each of the components of the signal; and
determining a relative loudness of a target signal within each component of a first portion of the audio signal compared to a relative loudness of a second portion of the received signal, wherein the stimulation level of each control signal is determined on the basis of the determined relative loudness of the corresponding target signal.

24. The method of claim 22, further comprising analyzing each of the components of the signal and determining informational content of the analyzed component of the signal, wherein the stimulation level of each control signal is determined on the basis of the determined informational content of the corresponding signal component.

25. The method of claim 20, which further includes analyzing each of the components of the signal and using a heuristic process to determine a stimulation level of each stimulation signal.

* * * * *